United States Patent [19]

Schultz

[11] Patent Number: 5,139,958
[45] Date of Patent: Aug. 18, 1992

[54] METHOD AND DEVICE FOR THE DETERMINATION OF LOW CONCENTRATIONS OF OXYGEN IN CARBONACEOUS MATERIALS

[75] Inventor: Hyman Schultz, Jefferson Boro, Pa.

[73] Assignee: The United States of America as represented by the United States Department of Energy, Washington, D.C.

[21] Appl. No.: 765,079

[22] Filed: Sep. 24, 1991

[51] Int. Cl.$^5$ ............................................. G01N 31/12
[52] U.S. Cl. ....................................... 436/136; 436/59; 436/127; 436/155; 422/80
[58] Field of Search ................ 422/78, 80, 98; 377/11, 377/12; 436/52, 59, 127, 136, 155

[56] References Cited

U.S. PATENT DOCUMENTS

| | | | |
|---|---|---|---|
| 3,374,064 | 3/1968 | Kolsto | 436/136 |
| 4,601,882 | 7/1986 | Benner | 422/80 |
| 4,741,817 | 5/1988 | Croset et al. | 204/425 |
| 4,744,805 | 5/1988 | Maroulis et al. | 55/66 |
| 4,800,747 | 1/1989 | Tsuji et al. | 73/19 |

Primary Examiner—James C. Housel
Assistant Examiner—David Redding
Attorney, Agent, or Firm—Hugh W. Glenn; Robert J. Fisher; William R. Moser

[57] ABSTRACT

Oxygen in carbonaceous materials is converted to carbon monoxide (CO) by pyrolyzing the material in a stream of oxygen-free helium. The CO is reacted with $Ni^{63}$, a readioactive isotope of nickel, to form nickel tetracarbonyl ($Ni^{63}(CO)_4$) which is carried by the helium stream into a flow-through gas proportional counter. The quantity of $Ni(CO)_4$ is determined by the radioactivity of the gas as measured by the gas proportional counter. After exiting the flow through counter the $Ni^{63}(CO)_4$ is destroyed by exposing it to high temperatures. The $Ni^{63}$ is retained within the apparatus while the CO is flushed from the system after being oxidized to carbon dioxide ($CO_2$). The detection limit is estimated to be less than 1 part per billion oxygen for a 10 mg sample.

17 Claims, 2 Drawing Sheets

METHOD AND DEVICE FOR THE DETERMINATION OF LOW CONCENTRATIONS OF OXYGEN IN CARBONACEOUS MATERIALS

CONTRACTUAL ORIGIN OF THE INVENTION

The United States Government has rights in this invention pursuant to the employer/employee relationship of the inventor to the U.S. Department of Energy at the Pittsburgh Energy Technology Center.

BACKGROUND OF THE INVENTION

This invention relates to generally analyzing gaseous and solid materials, and in particular to components containing oxygen, and more particularly to an oxygen analyzer capable of quantifying microgram quantities of oxygen.

Numerous methods and apparatus have been developed for the analysis of matter, particularly by different types of pyrolysis ovens utilizing various types of sample holding structures and product evaluation techniques. These prior know approaches are exemplified by U.S. Pat. Nos. 1,515,237 issued Nov. 11, 1924 to T. D. Yensen; 3,252,759 issued May 24, 1966 to W. Simon; 3,374,065 issued Mar. 19, 1968 to O. L. Kolsto; 3,861,874 issued Jan. 21, 1975 to A. E. Krc; 4,244,917 issued Jan. 13, 1981 to R. A. Woods et al; 4,800,747 to T. S. Uji et al; 4,744,805 to Maroulis et al; and 4,741,817 to Croset et al.

There are currently two known and established procedures, either of which may be used in analyzing devices. The most common of these two processes involves a system in which a weighted sample is placed in a quartz pyrolysis tube containing platinized carbon. Oxygen in the gaseous combustion products are converted to carbon monoxide by passage through the platinized carbon and the carbon monoxide is subsequently oxidized to carbon dioxide by passage over copper oxide. The sample is pyrolyzed in a helium atmosphere so that carbon monoxide is formed from oxygen in the sample and so that the platinized carbon does not burn. The carbon monoxide is oxidized by the copper oxide to form carbon dioxide, which is detected and measured, giving the total oxygen concentration in the sample. This procedure or process may, for example, be carried out in a Perkin-Elmer Model 240 Elemental Analyzer made by Perkin-Elmer Corp., Norwalk, Connecticut, which incorporates features of above-referenced U.S. Pat. No. 3,252,759.

The other of these procedures or processes uses the normal inert gas-fusion method as a basis for determining oxygen released at successively higher temperatures. The sample is heated in a graphite crucible, current is increased in discrete steps using a program tailored for the specific oxides believed to be present. The oxygen peaks are plotted against temperature on an integral printer, yielding information about individual compounds present in the sample. This process may, for example, be carried out in a LECO RO-16 Oxygen Determinator, made by LECO Corp., St. Joseph, Mich.

While the above-referenced processes and apparatus have been effective, they have been found to lack the necessary sensitivity for certain types of analysis. Thus, a need exists for an oxygen analysis procedure and apparatus which provides greater sensitivity than the currently know approaches.

U.S. Pat. No. 4,601,882 discloses an oxygen analyzer which identifies and classifies microgram quantities of oxygen and ambient particulate matter and for quantitating organic oxygen in solvent extracts of ambient particulate matter. A sample is pyrolyzed in oxygen free nitrogen gas and the resulting oxygen quantitatively converted to carbon monoxide by contact with hot granular carbon. Two analysis modes are made possible; 1) rapid determination of total pyrolyzable oxygen obtained by decomposing the sample at 1135° C. or 2) temperature programed oxygen thermal analysis obtained by heating the sample from room temperature to 1135° C. as a function of time. The analyzer basically comprises a pyrolysis tube containing a bed of granular carbon under $N_2$, ovens used to heat the carbon and or decompose the sample in a non-dispursive infrared CO detector coupled to a minicomputer to quantitate oxygen in the decomposition products and control oven heating. However, it has been found that the resulting analyzer lacks the necessary sensitivity for certain types of analysis.

SUMMARY OF THE INVENTION

Accordingly, a device and method are provided for determining low concentrations of oxygen in samples of carbonaceous material. The device includes a platinum tube and a mechanism for introducing the sample of carbonaceous material into the tube. A first clamshell furnace is disposed about a first section of the tube which is used by pyrolyzing or heating the sample so as to produce carbon monoxide. A coating of carbonaceous material, in a preferred embodiment being hydrocarbon gas or liquid, is coated on the interior walls of the first section of the tubing so as to bond the carbon to oxygen released from the sample during pyrolyzing, thereby forming carbon monoxide. The tube is continuously flushed with helium so as to prevent the oxygen from the air contaminating the samples or interacting with the carbonaceous material A second clamshell furnace is disposed about a second section of the tube. The second section of the tube contains radioactive nickel[63] for reacting under heat with the carbon monoxide to form nickel tetracarbonyl. The pressure of the helium forces the carbon monoxide from the first section into the second section. A flow-through gas counter measures the quantity of the nickel tetracarbonyl therein thereby indicating the quantity of oxygen in the sample. By comparing the quantity of the sample originally admitted into the tubing to the oxygen determined by the radioactivity, the concentration of oxygen in the sample may thereby be determined. Following measuring of the radioactivity, the nickel tetracarbonyl is flushed from the second section into a third section and into a fourth sections of the tubing. A third clamshell furnace is disposed about the fourth section of the tube, for heating the nickel tetracarbonyl and reducing it back to nickel[63] and carbon dioxide. The nickel[63] is returned to the second section of the tube. The carbon monoxide is flushed to a fifth section of the tube where a fourth clamshell furnace is disposed The carbon monoxide is then heated in the presence of copper oxide to form carbon dioxide which is released to the atmosphere.

DETAILED DESCRIPTION OF THE PREFERRED EMBODIMENT

Figure 1:
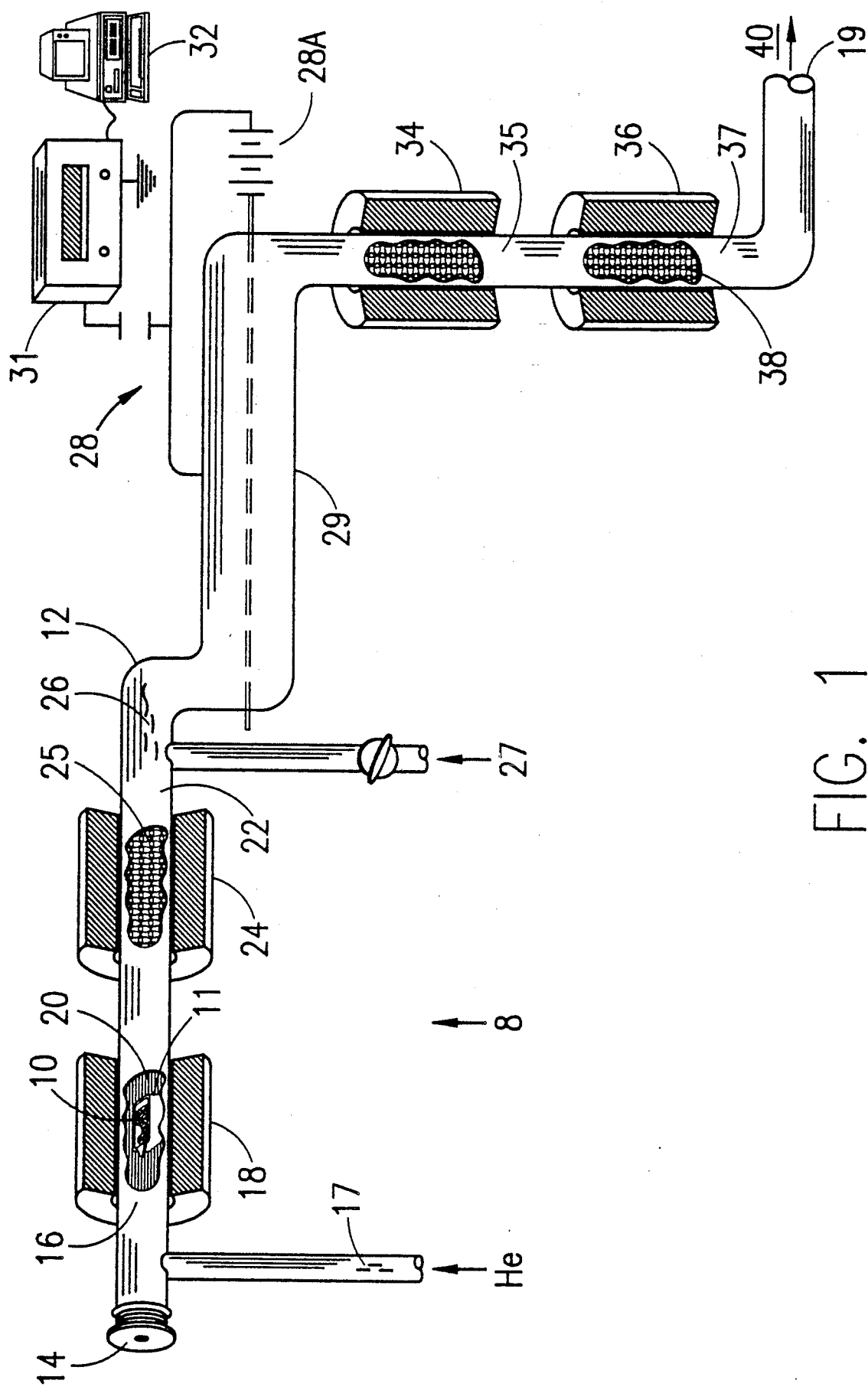
FIG. 1 of the drawings is front perspective vie partially broken away of a device for determining oxygen concentrations of carbonaceous material.

While the present invention is susceptible of embodiment in many different forms, there is shown in the drawings and will herein be described in detail several specific embodiments with the understanding that the invention is not limited thereto except in so far as those who have the disclosure before them are able to make modifications and variations therein without departing from the scope of the invention.

As shown in FIG. 1, a device 8 is provided for determining concentrations of oxygen in samples. An injection cap 14 is provided for entry of the sample 10. A sample 10 is placed (in a boat 11 or injected) into a platinum tube 12. A first section 16 of the tube 12 is heated at a temperature of 1000° C. to 1100° C. by means of a first clamshell furnace 18. The tube 12 is continuously flushed with oxygen free helium 17 from a helium source (not shown) under pressure. The tube walls 19 of first section 16 are be precoated with carbon 20 by injecting several samples of a suitable carbonaceous material such as a hydrocarbon gas or liquid.

The sample 10 is pyrolyzed in the first furnace 18 and the oxygen in the sample 10 reacts with the carbonaceous materials 20 to form carbon monoxide (CO) either directly or by reduction of $CO_2$ if that is initially formed. The carbon monoxide is then flushed into a second section 22 of tube 12 which is kept at approximately 100° C. A second clamshell furnace 24 is disposed about second section 22. Section 22 contains radioactive $Ni^{63}$ 25 arranged in such a manner as to allow maximum contact with the carrier gas without preventing its free flow (mossy nickel formed into a steel wool like configuration). In this second furnace 24 the CO reacts with the $Ni^{63}$ (a radioactive isotope of nickel with a reported half-life of 92 years) to form nickel tetracarbonyl, $[Ni^{63}(CO)_4]$. Nickel tetracarbonyl 26 is volatile with a boiling point between 40° C. and 50° C. In order to keep the nickel tetracarbonyl 26 in the vapor state the entire apparatus is kept at temperatures between 50° C. and 70° C. after the point where the nickel tetracarbonyl 26 is formed.

The nickel tetracarbonyl 26 is flushed into a flow-through gas counter 28 about third section 29 of tube 12 with the provision for adding a quenching agent at 27 if required. (For ultimate sensitivity the nickel tetracarbonyl could be added to a static gas proportional counter at 28A to allow for longer counting times.) The flow-through counter 28 is connected to a high voltage supply which is set so that the counting is done in the proportional region. The sign of the pulses is proportional to the energy of the detection. The number of pulses is proportional to the quantity of radioactive nickel. The output pulses of the counter are fed to a count rate meter and integrator or to a multi-channel analyzer 31. The electronics of the integrator have upper and lower energy gates to isolate the pulses due to the electrons emitted by the $Ni^{63}$. A readout device such as a strip chart recorder or microcomputer 32 is attached to the analyzer 31. The total activity of the $Ni^{63}(CO)_4$ is determined by integrating the radioactive peak that passes through the flow-through counter 28. The total activity detected is proportional to the quantity of $Ni^{63}(CO)_4$ and therefore to the quantity of oxygen in the sample.

After passing through the counter 28 the gas stream enters a third furnace 34 disposed about the fourth section 35 of tube 12. Furnace 34 is held at a temperature of about 1000° C. so the $Ni^{63}(CO)_4$ will decompose. The $Ni^{63}$ remains in the third furnace 34 while the CO passes to a fourth furnace 36 disposed about a fifth section 37 of tube 12. Fifth section 37 contains a suitable oxidizing agent such as copper oxide 38 where it is converted to $CO_2$ and flushed to the atmosphere 40.

CALCULATIONS

For a radioactive material, $$-dN/dt = \lambda N,$$

where N is the number of atoms of the radioactive isotope, $\lambda$ is the decay constant and $-(dN/dt)$ is the decrease in the number of radioactive atoms with time due to radioactive decay.

Integrating, the expression becomes, $$\ln N_o/N = \lambda(t - t_o),$$

where $N_o$ is the number atoms at the start ($t_o$) and N is the number at times T. At the half life, $T_{\frac{1}{2}}$, $$N = \tfrac{1}{2} N_o,$$

and the expression becomes $$\ln 2 = \lambda t_{\frac{1}{2}}.$$

Solving for $\lambda$ and substituting the half life of $Ni^{63}$ in seconds.

$$\lambda = \frac{0.693}{(92)(365)(24)(60)(60)} = 2.39 \times 10^{-10} \, \text{sec}^{-1}$$

The decay rate for one gram-mole of $Ni^{63}$ would be;

$$-\frac{dN}{dt} = N =$$

$$(2.39 \, \text{sec}^{-1} \times 10^{-10})(6.023 \, \text{atoms per mole} \times 10^{-23}) =$$

$$1.44 \times 10^{14} \, \text{disintegrations, per second (dps)}$$

Each gram-mole of $Ni^{63}$ is associated with four (4) grammoles of oxygen, therefore each gram-mole of oxygen is associated with $3.6 \times 10^{13}$ dps. If we assume a detection limit of 10 counts per second, a sample size of 10 milligrams and a 50% detection efficiency the minimum concentration of oxygen detectable would be:

$$\frac{\left(\frac{10 \, dps}{0.5}\right)\left(\frac{1}{3.6 \times 10^{13} \, dps}\right)(16 \, \text{gm O/gm} - \text{mole})}{1 \, 10^{-3} \, g} =$$

(0.9 parts per billion)

A larger sample, a lower detection limit for the count rate or a higher detection efficiency could lower the stated limit of detection for oxygen by this method to less than one part per billion.

Platinum tubing 12 is preferably a quarter inch in diameter having sidewalls of 0.010. The platinum acts as a catalyst in a reaction between the hydrocarbon and the sample so as to facilitate formation of carbon monoxide. Each reaction section, sections 16, 22, 29, 35 and 37 are approximately one (1) foot in length. Furnaces 18, 24, 34 and 36 are conventional electrical resistance heating clamshell type furnaces as found in the Fisher and Scientific Catalog. Preferably the furnaces are 110 volt AC utilizing up to 1000 watts of current.

As noted above, counting of the radioactivity present in the nickel tetracarbonyl is done in the proportional region of count rate meter. By this it is meant that as energy is increased in the gas counter 28, the activity reaches what is called the geiger region, where there is an avalanche of electrons from the sample. Thus it is more difficult to take meaningful readings at this point. In the proportional region where a lower quantity of potential energy is provided, the pulses of radioactivity are proportional to the energy coming in so that you can isolate the electrons due to nickel$^{63}$. In a preferred embodiment the quenching agent 26 comprises ethanol. The quenching agent 26 prevents continuous discharge of electrons so as to quench the pulses of radioactivity. Finally, in a preferred embodiment the gas counter 28 is a standard radioactive gas counter manufactured by Baird Atomic, or equivalent.

Figure 2:
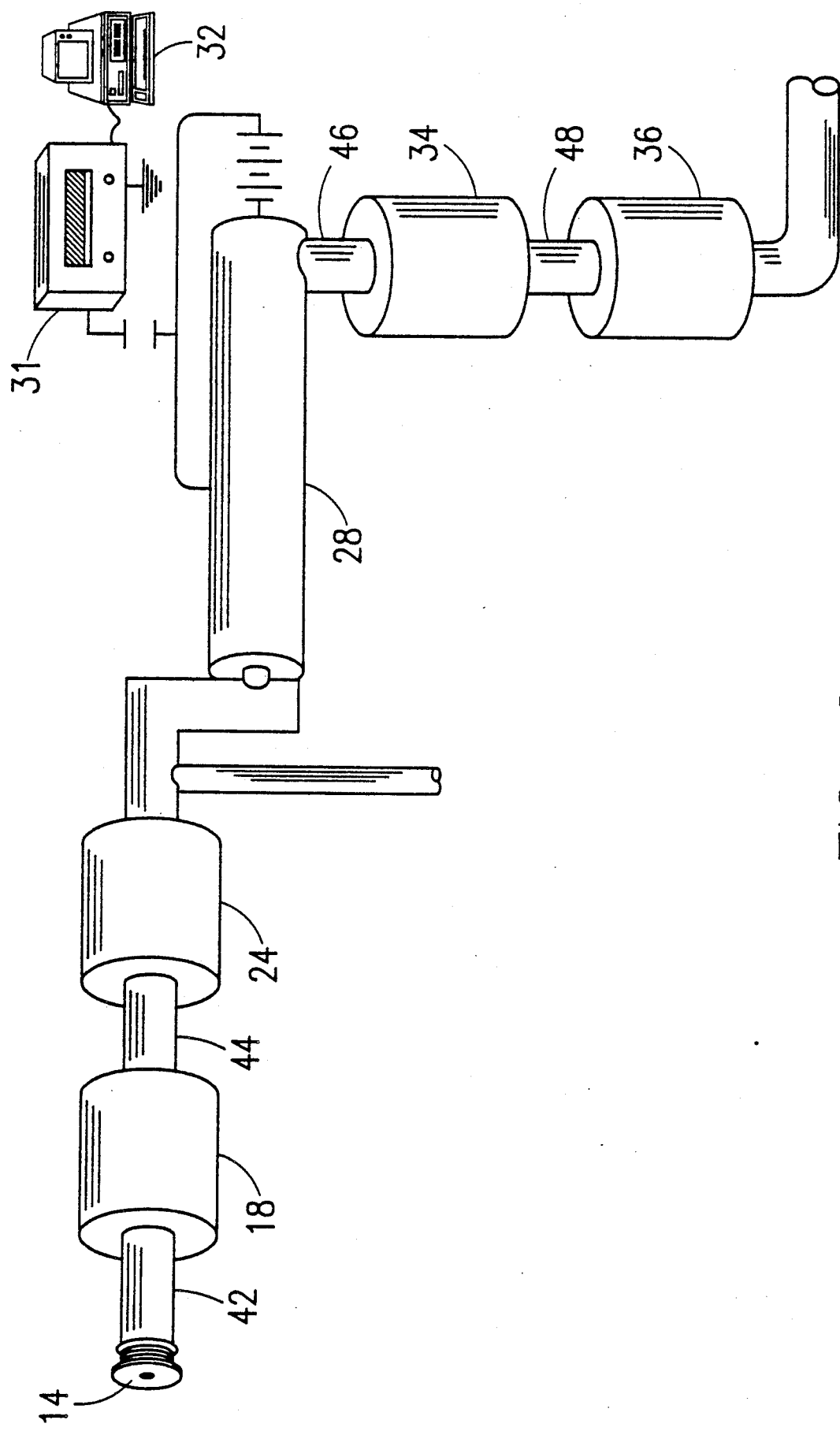
FIG. 2 of the drawings is a front perspective view of an alternate embodiment of the invention of FIG. 1 in which individual furnaces are interconnected by sections of tubing and in turn a section of tubing extends a through a separate gas counter.

As shown in FIG. 2 of the drawing, in an alternate embodiment, first furnace 18, second furnace 24, third furnace 34 and fourth furnace 36 are not clamshell in design, but are formed as stand alone units having individual section of platinum tubing contained therein. Each of the furnaces in turn is connected by sections 42, 44, 46 and 48 respectively of platinum tubing. As a result, the heating chamber of each furnace may be designed so as to maximize the chemical reaction desired in that section of the furnace.

The embodiment of the invention in which an exclusive property or privilege is claimed is defined as follows:

1. A device for the determination of concentrations of oxygen in samples of carbonaceous materials, said device comprising:
    a platinum tube;
    means for introducing said samples within said tube;
    a first clamshell furnace disposed about a first section of said tube constructed so as to pyrolyze said samples to produce carbon monoxide;
    a coating of carbonaceous material arranged on the interior walls of said first section for bonding to oxygen in said samples to form said carbon monoxide;
    means for flushing said first section of said tube with oxygen free helium so as to prevent oxygen from air from contaminating said sample;
    a second clamshell furnace disposed about a second section of said tube, said second section of said tube containing Nickel$^{63}$ for reacting at high temperatures with said carbon monoxide to form nickel tetracarbonyl;
    means for flushing said carbon monoxide from said first section of said tube into said second section of said tube;
    a flow through gas counter disposed about a third section of said tube for constructed so as to measure the quantity of nickel tetracarbonyl therein, thereby indicating the quantity of oxygen in said sample;
    a third clamshell furnace disposed about a fourth section of said tube for constructed so as to decompose said nickel tetracarbonyl to form nickel$^{63}$ and carbon monoxide wherein said nickel remaining in said fourth section is recycled for later use; and
    means for flushing said nickel tetracarbonyl from said second section through said third section and into said fourth section;
    a fourth clamshell furnace disposed about a fifth section of said tube said fifth section containing an oxidizing agent that converts carbon monoxide to carbon dioxide for release to the atmosphere.

2. A device for determination of oxygen concentration in samples of carbonaceous materials, said device comprising:
    means for pyrolyzing said samples in an inert helium environment and in the presence of pure carbonaceous material so as to produce carbon monoxide;
    means for causing the interacting of said carbon monoxide with nickel$^{63}$ so as to produce nickel tetracarbonyl; and
    means for measuring the quantity of nickel tetracarbonyl produced in relation to the quantity of said samples so as to determine the concentration of oxygen in said samples.

3. The device of claim 2 wherein said means for pyrolyzing said samples comprises:
    a first clamshell furnace disposed about a first section of said tube constructed so as to pyrolyze said samples to produce carbon monoxide.

4. The device of claim 2 wherein said means for causing the interaction of said carbon monoxide with said nickel$^{63}$ comprises:
    a second clamshell furnace disposed about a second section of said tube, said second section of said tube containing Nickel$^{63}$ for reacting at a high temperature with said carbon monoxide to form nickel tetracarbonyl.

5. The device of claim 1 wherein said means for measuring the quantity of nickel tetracarbonyl comprises:
    a flow through gas counter means.

6. The device of claim 5 wherein said flow through gas counter means comprises:
    means for adding a quenching agent so as to quench radioactivity of said sample.

7. The device of claim 3 wherein said means for measuring the quantity of nickel tetracarbonyl comprises:
    a static gas proportional counter means so as to allow for longer counting times and thereby increased sensitivity.

8. The device of claim 5 wherein said flow through gas counter means comprises:
    a high voltage supply;
    a count rate meter;
    a multi-channel analyzer having upper and lower energy gates to isolate the pulses due to electrons emitted by Ni$^{63}$;
    an integrator constructed so as to integrate radioactive peaks which reflect the flow of nickel tetracarbonyl that pulses through the flow-through counter means; and
    a readout device for displaying the total radioactive activity.

9. The device of claim 2 wherein said means for pyrolyzing said samples comprises:
    a first furnace means having a coating of carbonaceous material;
    said means for causing the interaction of said carbon monoxide with nickel$^{63}$ comprises a second furnace means interconnected by means of tubing with said first furnace means; and said means for measuring comprises a flow-through radioactive gas counter interconnected by means of tubing with said second furnace means.

10. The device of claim 1 wherein said means for flushing said first section of said tube comprises a valved tubular inlet connected to a source of pure helium under pressure.

11. The device of claim 1 wherein said means for introducing sample comprises a boat containing said sample and a chamber means for introducing said boat containing a sample in an environment of pure helium.

12. The device of claim 1 wherein said means for introducing said samples comprises an injection valve means for injecting said samples under pressure into said platinum tube.

13. A method of determining the concentration of oxygen in samples of carbonaceous material utilizing first and second tubular clamshell furnace, helium, $Ni^{63}$ and a gas counter means comprising:

coating the interior of a first clamshell furnace with carbonaceous material;

continuously flushing said first furnace with helium;

placing sample of said carbonaceous material into said first furnace;

pyrolyzing said sample in the presence of said helium so as to produce carbon monoxide;

flushing the carbon monoxide into said second clamshell furnace;

admitting $nickel^{63}$ into said second clamshell furnace;

heating said carbon monoxide in said second clamshell furnace so as to produce nickel tetracarbonyl;

flushing said nickel tetracarbonyl into said gas counter means;

measuring the quantity of nickel tetracarbonyl present; and determining thereby the oxygen concentration in the sample.

14. The method of claim 13 wherein said step of coating said first clamshell furnace comprises:

injecting a sample of said carbonaceous material into said first clamshell furnace.

15. The method of claim 13 wherein said step of pyrolyzing said sample comprises:

heating said sample at a temperature of 1050° C. ±50°.

16. The method of claim 13 wherein said step of heating said carbon monoxide comprises: maintaining the temperature of said nickel tetracarbonyl at a temperature of between 40° C. and 50° C. so as to remain in the vapor state.

17. The method of claim 13 wherein said step of measuring the quantity of nickel tetracarbonyl comprises:

counting the number of output pulses of said gas counter;

isolating the pulses caused by the electrons of the $nickel^{63}$;

integrating the radioactive peaks as a result of the nickel tetracarbonyl passing through the gas counter means; and calculating the quantity of nickel tetracarbonyl.

* * * * *